United States Patent [19]
Einsele et al.

[11] Patent Number: 6,046,006
[45] Date of Patent: Apr. 4, 2000

[54] SEQUENTIAL HYBRIDIZATION OF FUNGAL CELL DNA AND METHOD FOR THE DETECTION OF FUNGAL CELLS IN CLINICAL MATERIAL

[75] Inventors: Hermann Einsele, Tubingen; Jürgen Löffler, Reutlingen, both of Germany

[73] Assignees: Eberhard-Karls-Universitat; Tubingen Universitatsklinikum, both of Tubingen, Germany

[21] Appl. No.: 09/242,797

[22] PCT Filed: Jul. 11, 1997

[86] PCT No.: PCT/EP97/03687

§ 371 Date: Apr. 26, 1999

§ 102(e) Date: Apr. 26, 1999

[87] PCT Pub. No.: WO98/08972

PCT Pub. Date: Mar. 5, 1998

[30] Foreign Application Priority Data

Aug. 31, 1996 [DE] Germany ............................ 196 35 347

[51] Int. Cl.$^7$ .............................. C12Q 1/68; C07H 21/04; C12N 15/11
[52] U.S. Cl. .............................. 435/6; 536/23.1; 536/24.3
[58] Field of Search .......................... 435/6, 91.1, 254.1; 536/23.1, 24.1, 24.3, 24.33

[56] References Cited

FOREIGN PATENT DOCUMENTS

| | | |
|---|---|---|
| 0 422 869 A2 | 10/1990 | European Pat. Off. |
| 195 30 336 | 2/1997 | Germany. |
| WO 91/02092 | 2/1992 | WIPO. |
| WO 96/21741 | 7/1996 | WIPO. |
| WO 97/07238 | 2/1997 | WIPO. |

OTHER PUBLICATIONS

Kobayashi, et al., Simple detection f the 5S ribosomal RNA of *Pneumocystis carinii* using in situ hybridisation, Journal of Clinical Pathology, 49(9) (1996) 712–716. (abstract).

Shah, et al., Diversity of host species and strains of *Pneumocystis carini* is based on rRNA sequences, Clinical and Diagnostic Laboratory Immunology, 3(1) (1996) 119–127. (abstract).

De Luca, et al., Variable efficiency of three primer pairs for the diagnosis of *Pneumocystis carinii* pneumonia by the polymerase chain reaction, Molecular and Cellular Probes, 9(5) (1995) 333–340. (abstract).

Lu, et al., Typing of *Pneumocystis carinii* strains with type–specific oligonucleotide probes derived from nucleotide sequences of internal transcribed spacers of Rrna genes, Journal of Clinical Microbiology, 33(11) (1995) 2973–2977. (abstract).

Mazars, et al., Polymorphism of the thymidylate synthase gene of *Pneumocystis carinii* from different host species, Journal of Eukaryotic Microbiology, 42(1) (1995) 26–32. (abstract).

van Belkum, et al., Monitoring spread of Malassezia infections in a neonatal intensive care unit by PCR–mediated genetic typing, Journal of Clinical Microbiology, 32(10) (1994) 2528–2532. (abstract).

Borensztein, et al., An alternative to DNA extraction for the diagnosis of *Pneumocystis carinii* pneumonia by polymerase chain reaction using a new oligonucleotide probe, Molecular and Cellular Probes, 6(5) (1992) 361–365 (abstract).

Peters, et al., Quantification of the detection of *Pneumocystis carinii* by DNA amplification, Molecular and Cellular Probes, 6(2) (192) 115–117 (abstract).

Wakefield, et al., Detection of *Pneumocystis carinii* with DNA amplification, Lancet, 336 (8713) (1990) 451–453. (abstract).

XP002046318—Lu, et al., Comparison of Six Different PCR Methods for Detection of *Pneumocystis carinii*, Journal of Clinical Microbiology, Oct. 1995, pp. 2785–2788.

XP002045921—Edman, et al., Ribosomal RNA sequence shows *Pneumocystis carinii* to be member of the Fungi, Letters to Nature, vol. 334, Aug. 11, 1998, pp. 519–522.

XP002046319—Belkum, et al., Monitoring Spread of Malassezia Infections in a Neonatal Intensive Care Unit by PCR–Mediated Genetic Typing, Journal of Clinical Microbiology, Oct. 1994, pp. 2528–2532.

XP002045920—De Peer, et al., Evolution of Basidiomycetous Yeasts as Deduced from Small Ribosomal Subunit RNA Sequences, System. Appl. Microbiol., 15, pp. 250–258 (1992).

XP002046483—Glenn, et al., Molecular phylogeny of Acremonium and its taxoniomic implications, Mycologia, 88(3), 1996, pp. 369–383.

XP002046484—Spatafora, et al., Molecular Systematics of Unitunicate Perithecial Ascomycetes: The Clavicipitales–Hypocreales Connection, Mycolgia, 85(6), 1993, pp. 912–922.

XP002046485—Spatafora, et al., The Polyphyletic origins of ophiostomatoid fungi, Mycol. Res 98 (1) 1–9 (1994).

XP002046486—Makimura, et al., Detection of a wide range of medically important fungi by the polymerase chain reaction, J. Med. Microbiol., vol. 40 (1994), pp. 358–364.

XP002046322—Spatafora, et al., Petriella setifera small subunit rRNA, partial sequence, GenBank U32421, Mycol. Res. 98:1–9 (1994).

XP002046320—Glenn, et al., Myriogenospora atramentosa 18S, partial sequence, GenBank U44115, Mycologia 88:369–383 (1996).

XP002046321—Spatafora, et al., Balsansia sclerotica small subunit rRNA, partial sequence, GenBank U32399, Mycologia 85:912–922 (1993).

*Primary Examiner*—George C. Elliott
*Assistant Examiner*—Melissa Schmidt
*Attorney, Agent, or Firm*—Cummings & Lockwood; Steven J. Moore

[57] ABSTRACT

A method and kit for detecting fungal cells in clinical material utilizing nucleic acid hybridization probes identified as SEQ. ID NO. 9–12.

16 Claims, No Drawings

SEQUENTIAL HYBRIDIZATION OF FUNGAL CELL DNA AND METHOD FOR THE DETECTION OF FUNGAL CELLS IN CLINICAL MATERIAL

RELATED APPLICATIONS

This application claims benefit from PCT International Application PCT/EP97/03687, filed Jul. 11, 1997, wherein the United States was a designated country.

BACKGROUND OF THE INVENTION

1. Field of the Invention

The present invention relates to a method for detecting fungal cells in clinical material.

Methods for detecting fungal cells in clinical material are of great interest because, especially in recent years, fungal species have acquired considerable importance as significant nosocomial pathogens, in particular for immunosuppressed patients. If fungal infections are not recognized in time in such patients, they propagate in the patient's body and result in a high mortality rate. Treatment success can be improved only by timely diagnosis.

2. Related Prior Art

The standard methods known for the detection of fungal infections, which are based on the culturing of isolated fungi, are complex and time-consuming. On the other hand, fungal infections can be detected sensitively and promptly using new techniques based on molecular biology methods. These methods require, however, the ability to efficiently extract fungus-specific nucleic acids from clinical material. In order to identify, from these extracted nucleic acids, the fungal species responsible for the infection, specific sequences of different pathogenic fungal species must be known. This requires differentiating among the various fungal species, since the particular therapy depends on the individual fungal infection.

With this background, a method has been developed with which fungal DNA can be extracted from patient material, the fungal DNA can be analyzed, and various fungal species can be identified on the basis of the extracted DNA. This method is described in DE Patent Application 195 30 336.9 as follows:

First the fungal DNA is extracted from the patient's whole blood. This is done by first isolating fungal cells from blood cells. Then the fungal cells are lysed and their DNA is purified from the lysate. Fungus-specific DNA segments from the fungal cell DNA thus obtained is amplified in a polymerase chain reaction (PCR). This polymerase chain reaction is performed with two primers which amplify a region, comprising approximately 500 nucleotides, from the gene for 18ssu rRNA. The primers are selected so as to amplify only the corresponding gene region from fungi, but not gene regions from other organisms, for example the patient's own body cells. The sequences of these primers are listed in the attached Sequence Listing as SEQ ID No. 1 and 2.

A DNA fragment is thus amplified in the polymerase chain reaction only if a fungal infection is present. Considered in and of itself, the PCR thus serves to detect the existence of an infection with pathogenic fungi.

In order then to differentiate among different fungal species, the amplified 500-base-pair fragment is hybridized with one or more of a total of six probes. Each probe is specific for one fungal species. According to DE Patent Application 195 30 336.9, specific probes are indicated for a total of five Candida species and the genus Aspergillus. The probes are also listed in the Sequence Listing attached hereto, as SEQ ID No. 3 through 8.

The fungal genera Candida and Aspergillus are those by far most often involved in nosocomial infections. Less-common fungal species, for which so far no detection methods are available, are nevertheless also gaining in clinical significance.

SUMMARY OF THE INVENTION

Therefore, it is an object of the present application to provide for species-specific probes for the hitherto unknown rRNA gene region of uncommon fungal species. These probes have already been successfully used experimentally for the detection of the uncommon fungal species.

The sequences of these probes are listed in the attached Sequence Listing as SEQ ID No. 9, 10, 11, and 12.

The probe with the nucleotide sequence SEQ ID No. 9 is used to detect the fungal species *Pneumocystis carinii*. The probe with the nucleotide sequence SEQ ID No. 10 is used to detect the species *Malassezia furfur*. The letter K at position 21 stands for "G or T"; i.e. there are strains which require the G base here, and strains which require the T base here. The probe with the nucleotide sequence SEQ ID No. 11 is used to detect the species *Trichosporon cutaneum* and *Trichosporon capitatum*. Lastly, the probe with the sequence SEQ ID No. 12 is used to detect the fungal species *Fusarium solani* and *Fusarium oxysporum*.

Using these specific probes, it is possible for the first time to make even the uncommon pathogenic fungal species Pneumocystis, Malassezia, Trichosporon, and Fusarium accessible to a prompt, sensitive, and easily performed molecular biology detection method.

It is preferred in this context if these probes are utilized in a method of the kind described in DE Patent Application 195 30 336.9 described above. After extraction of the fungal DNA from clinical material and detection of the extracted fungal DNA via a polymerase chain reaction with primers SEQ ID No. 1 and 2, the probes presented here (SEQ ID No. 9 through 12) can be used as hybridization probes directly on the DNA fragment amplified in the PCR. It is possible in this context to use them individually, or in a sequential hybridization method together with the probes described in DE Patent Application 195 30 336.9.

It is understood, however, that the probes described here can also be used in other analysis methods, for example in a direct hybridization of total fungal DNA or fungal RNA, or as a primer for polymerase chain reactions.

Provision is also made for integrating the specific probes presented here into a kit with which fungal species can be identified. The kit can contain either only the DNA probes or also additional necessary solutions, thus considerably simplifying the everyday laboratory work of identifying the particular fungal species.

It is also possible, in this context, to include in a kit all the essential solutions for performing a method of the kind cited above. It can contain not only the probes specific for the uncommon fungal species, but also the probes described in DE Patent Application 195 30 336.9 for identifying Candida and Aspergillus species.

DESCRIPTION OF PREFERRED EMBODIMENTS

The Examples below illustrate the entire method for extracting fungal DNA from clinical material, detecting the extracted fungal DNA by polymerase chain reaction, and determining the fungal species from the extracted DNA.

Examples 1 and 2 illustrate how fungal cells can be obtained from blood cells contained in whole blood. Example 3 explains how predominantly intact fungal cells can be separated from cellular human DNA; Example 4 shows how fungal cells are disintegrated, and Example 5 shows how the fungal DNA is then isolated. Example 6 describes how the aforesaid fungus-specific 500-base-pair fragment from the gene region for 18ssu rRNA is amplified by polymerase chain reaction. Examples 7 and 8 demonstrate how the fungus-specific probes can be used to identify individual fungal species.

EXAMPLE 1

Lysis of Red Blood Cells by Osmotic Hemolysis

Red blood cells are lysed with a hypotonic solution, using the following buffer with the following final concentrations:

| | |
|---|---|
| Tris pH 7.6 | 10 mM |
| $MgCl_2$ | 5 mM |
| NaCl | 10 mM |

The solution is incubated at room temperature for 10 minutes, and then centrifuged.

A volume of 3 ml of whole blood is sufficient for this first step.

EXAMPLE 2

Enzymatic Disintegration of White Blood Cells

The white blood cells, which may contain fungal cells, are carefully broken up by enzymatically treating the cells with Proteinase K (200 μg/ml) of the Boehringer Mannheim company, in the following buffer with the indicated final concentrations, in which the pellet from Example 1 is placed:

| | |
|---|---|
| Tris pH 7.6 | 10 mM |
| EDTA pH 8.0 | 10 mM |
| NaCl | 50 mM |
| SDS | 0.2% |
| Proteinase K | 200 μg/ml |

This buffer is incubated for two hours at 65° C.

EXAMPLE 3

Separation of Predominantly Intact Fungal Cells, Principally from Cellular DNA

Once the blood cells have been disintegrated as described in Examples 1 and 2 to release the cellular DNA, a centrifugation step at 5000 rpm is performed; this results in a considerable loss of cellular DNA, which does not sediment at this centrifuge speed.

The sediment now contains exclusively the free or released fungal cells, to which NaOH is added for further processing.

EXAMPLE 4

Disintegration of Fungal Cells

Next the fungal cells are lysed in alkaline solution and enzymatically treated to release the fungal DNA.

This involves first an alkaline lysing step with 200 μl 50 mM NaOH for 10 minutes at 95° C.

That is followed by a neutralization step with 1 M Tris-HCl (pH 7.0) and centrifuging at 5000 rpm for 10 minutes.

500 μl Zymolyase of JCN (300 μg/ml) is then added, and the solution is incubated at 37° C. for 60 minutes in order to enzymatically disintegrate the fungal cells.

500 μl Tris/EDTA and 50 μl 10% SDS are then added, and the solution is incubated at 65° C. for 20 minutes to denature the protein.

EXAMPLE 5

Isolation of Fungal DNA

The solution thus obtained contains fungal cell debris as well as free fungal DNA, which must now be isolated.

This is done by first precipitating the protein with 5 M potassium acetate, after which the supernatant is removed, and the DNA is precipitated by adding ice-cold isopropanol. This precipitation product is then used for the remaining process steps.

The process steps described in Examples 1 through 5 thus make it possible to extract from whole blood, in highly selective fashion, fungal DNA which is then present as a precipitate with very little cellular DNA contamination, so that the detection process which now takes place can be performed in very sensitive and highly specific fashion.

EXAMPLE 6

Amplification of a Fungus-specific DNA Segment

The purpose of this process step is first to determine whether any fungal DNA at all is present in the precipitate from the process step in Example 5. The fact that the DNA sequences cited in the Sequence Listing as SEQ ID No. 1 and 2 specifically bind to binding regions on the fungal gene for 18 ssu rRNA of many fungal strains and species is exploited here.

The inventors of the present application have recognized not only that this fungal gene has, in the various fungal strains and species, a sequence segment of this kind which is flanked by two binding regions for primers that are identical for all fungal strains and species; but also that the sequence of this segment for the various fungal strains and species is so different that it can be used to identify the individual fungal strains and species.

In this context, DNA sequence SEQ ID No. 1 binds to the sense strand, while DNA sequence SEQ ID No. 2 binds to the anti-sense strand, the spacing between the two binding regions being approximately 500 base pairs. These two DNA sequences SEQ ID No. 1 and SEQ ID No. 2 are thus suitable as primers for a polymerase chain reaction (PCR) which consequently generates a sufficient quantity of amplification products (amplicon) with a length of approximately 500 base pairs.

The PCR conditions are as follows:

Buffer (50 μl):
10 mM Tris (pH 9.6)
50 mM NaCl
10 mM $MgCl_2$

-continued

| | |
|---|---|
| 0.2 mg/ml BSA | |
| Polymerase | |
| 0.5 mM of each nucleotide | |
| 100 pM of each primer | |
| Initial denaturing: | 3 min at 94° C. |
| Cycle denaturing: | 0.5 min at 94° C. |
| Annealing: | 1 min at 62° C. |
| Extension: | 2 min at 72° C. |
| Terminal extension: | 5 min at 72° C. |
| No. of cycles: | 34 |

The high concentration of magnesium in the buffer ensures high specificity for the polymerase, which can operate in the extension step at its optimum temperature (72° C.).

EXAMPLE 7

Detection of the Amplification Products from Example 6

The next step is intended to determine whether the polymerase chain reaction in Example 6 has actually resulted in the amplification of DNA segments with a length of approximately 500 base pairs. This detection of fungus-specific DNA segments is performed by ethidium bromide staining of the specific band in a 2% agarose gel.

If the specific band is found there, it can be assumed that a fungal infection is present, since primers SEQ ID No. 1 and 2 bind to all the aforementioned fungal species. In other words, if the process steps in Examples 1 through 5 resulted in the extraction of fungal DNA, it is so far amplified by the PCR step of Example 6 that it can be detected here by ethidium bromide staining.

EXAMPLE 8

Assignment of the Amplification Products from Example 6 to Individual Fungal Species For specific therapy, it is now also necessary to specify more accurately the fungal infection already detected in step 7. This now reveals a further advantage of the PCR step of Example 6, namely that it generates so much fungus-specific DNA segment that further detection methods are possible so as to determine the fungal species.

This is done by utilizing the nucleotide sequences SEQ ID No. 3 through 12 listed in the Sequence Listing, which serve as species-specific probes that specifically hybridize with a sequence portion of the DNA segment generated in Example 6.

It has been found that probe SEQ ID No. 3 hybridizes with *Candida albicans*, SEQ ID No. 4 with *Candida glabrata*, SEQ ID No. 5 with *Candida krusei*, SEQ ID No. 6 with *Candida tropicalis*, SEQ ID No. 7 with *Candida parapsilosis*, and SEQ ID No. 8 with *Aspergillus fumigatus, A. flavus, A. versicolor, A. niger, A. nidulans*, and A. terreus. Nucleotide sequence SEQ ID No. 8 is thus a general Aspergillus probe, while nucleotide sequences SEQ ID No. 3 through 5 can distinguish among fungal species of the Candida genus.

Probe SEQ ID No. 9 hybridizes with *Pneumocystis carinii*, probe SEQ ID No. 10 with *Malassezia furfur*, probe SEQ ID No. 11 with *Trichosporon cutaneum* and *Trichosporon capitatum*, and probe SEQ ID No. 12 with *Fusarium solani* and *Fusarium oxysporum*. It should also be noted that in SEQ ID No. 10, K stands for "G or T".

In order to detect hybridization once it has occurred, the probes are marked with digoxigenin using the transferase kit of the Boehringer Mannheim company, detection being accomplished using the Southern Blot method with the usual color reaction.

It is thus possible in this fashion, by sequential hybridization based on the amplification products generated in the step of Example 6, to identify the fungal species and then to initiate specific therapy.

Therefore, what we claim, is:

1. A method for detecting and identifying fungus in clinical material, comprising the steps of:
   (a) extracting fungal DNA from clinical material;
   (b) detecting extracted fungal DNA;
   (c) determining the fungal species by hybridizing the extracted DNA with fungus specific probes, where one or more of the nucleotide sequences SEQ ID No. 9 through 12 are used as the fungus specific probes.

2. The method of claim 1, wherein in detecting the extracted fungal DNA, an amplification of a DNA segment is performed by a polymerase chain reaction (PCR) using the primers with the nucleic acid sequences SEQ ID No. 1 and SEQ ID No. 2.

3. A nucleic acid probe consisting of the sequence of SEQ ID No. 9.

4. A nucleic acid probe consisting of the sequence of SEQ ID No. 10.

5. A nucleic acid probe consisting of the sequence of SEQ ID No. 11.

6. A nucleic acid probe consisting of the sequence of SEQ ID No. 12.

7. The method of claim 1 wherein the fungus specific probe is nucleotide sequence SEQ ID No. 3 and the fungus identified is of the fungal species *Pneumocystis carinii*.

8. The method of claim 1 wherein fungus specific probe is nucleotide sequence SEQ ID No. 10 and the fungus identified is of the fungal species *Malassezia furfur*.

9. The method of claim 1 wherein the fungus specific probe is nucleotide sequence SEQ ID No. 11 and the fungus identified is of the fungal species *Trichosporon cutaneum* and/or *Trichosporon capitatum*.

10. The method of claim 1 wherein the fungus specific probe is nucleotide sequence SEQ ID No. 12 and the fungus identified is of the fungal species *Fusarium solani* and/or *Fusarium oxysporon*.

11. A kit for identifying fungal species, wherein the nucleotide sequence of claim 3 is contained as a probe.

12. A kit for identifying fungal species, wherein the nucleotide sequence of claim 4 is contained as a probe.

13. A kit for identifying fungal species, wherein the nucleotide sequence of claim 5 is contained as a probe.

14. A kit for identifying fungal species, wherein the nucleotide sequence of claim 6 is contained as a probe.

15. A kit for performing a method as defined in claim 1.

16. A kit for performing a method as defined in claim 2.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Binds to a
      region of a fungal 18 ssu rRNA gene

<400> SEQUENCE: 1
attggagggc aagtctggtg                                                      20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Binds to a
      region of a fungal 18 ssu rRNA gene

<400> SEQUENCE: 2
ccgatcccta gtcggcatag                                                      20

<210> SEQ ID NO 3

<211> LENGTH: 30
<212> TYPE: DNA
<213> ORGANISM: Artificial Sequence
<220> FEATURE:
<223> OTHER INFORMATION: Description of Artificial Sequence: Binds to a
      region of a fungal 18 ssu rRNA gene

<400> SEQUENCE: 3
tctgggtagc catttatggc gaaccaggac                                    30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Binds to a
      region of a fungal 18 ssu rRNA gene

<400> SEQUENCE: 4
ttctggctaa ccccaagtcc ttgtggcttg                                    30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Binds to a
      region of a fungal 18 ssu rRNA gene

<400> SEQUENCE: 5
gtctttcctt ctggctagcc tcgggcgaac                                    30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Binds to a
      region of a fungal 18 ssu rRNA gene

<400> SEQUENCE: 6
gttggccggt ccatctttct gatgcgtact                                    30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Binds to a
      region of a fungal 18 ssu rRNA gene

<400> SEQUENCE: 7
tttccttctg gctagccttt ttggcgaacc                                    30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Binds to a
      region of a fungal 18 ssu rRNA gene

<400> SEQUENCE: 8
catggccttc actggctgtg gggggaacca                                    30

<210> SEQ ID NO 9
<211> LENGTH: 30

-continued

```
<212> TYPE: DNA
<213> ORGANISM: Artificial Sequence
<220> FEATURE:
<223> OTHER INFORMATION: Description of Artificial Sequence: Binds to a
      region of a fungal 18 ssu rRNA gene

<400> SEQUENCE: 9
attaccggct gcccttcgct gggtgtgccg                                         30

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Binds to a
      region of a fungal 18 ssu rRNA gene

<400> SEQUENCE: 10
agagtgttca aagcaggctt kacgcc                                             26

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Binds to a
      region of a fungal 18 ssu rRNA gene

<400> SEQUENCE: 11
aggccgtatg cccttcattg ggtgtgcggt                                         30

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Binds to a
      region of a fungal 18 ssu rRNA gene

<400> SEQUENCE: 12
tgctccaggc aggcctatgc tcga                                               24
```